United States Patent [19]

Shepard

[11] 4,407,842

[45] Oct. 4, 1983

[54] METHOD AND COMPOSITION FOR RAPIDLY DEVELOPING LATENT FINGERPRINTS

[76] Inventor: Billy H. Shepard, 170 MarBil Rd. (P.O. Box 225), Milton, Fla. 32570

[21] Appl. No.: 370,382

[22] Filed: Apr. 21, 1982

[51] Int. Cl.$^3$ ............................................... A61B 5/10
[52] U.S. Cl. .................................. 427/1; 106/287.25; 156/241; 252/374; 252/408.1; 427/145; 427/255.4
[58] Field of Search ........................ 427/1, 145, 255.4; 252/374, 408; 106/287.25; 156/241

[56] References Cited

U.S. PATENT DOCUMENTS 4,176,205  11/1979  Moling ..................................... 427/1
4,297,383  10/1981  Bourdon ................................. 427/1

*Primary Examiner*—Norman Morgenstern
*Assistant Examiner*—Janyce A. Bell
*Attorney, Agent, or Firm*—Harvey B. Jacobson

[57] ABSTRACT

A method of and composition for developing latent fingerprints on various surfaces including but not limited to glass, plastic, various metals such as copper, brass and the like and other materials such as paper which involves subjecting the latent fingerprints to gaseous fumes produced by cyanoacrylate ester, sodium bicarbonate and sulfur which will develop the latent fingerprints in a very short period of time thereby enabling the fingerprints to be easily lifted by conventional techniques for comparison with known fingerprints. The method of developing latent fingerprints of this invention may be used at the site of a crime by providing the fumes in a pressurized container so that the fumes can be directed into contact with the surface on which the latent fingerprints appear. The method is also effective at the laboratory by providing a container of sufficient size to receive the article or articles on which the fingerprints occur and a quantity of the composition which produces the fumes. The method and composition of the present invention develop latent fingerprints so that they are long lasting and can be lifted more than once if desired. Also, in lab use, by constructing the container for enabling articles to be quickly removed therefrom and additional articles placed therein, the fumes produced by a single batch of the composition can be used to develop latent fingerprints on several articles sequentially placed in the container.

17 Claims, No Drawings

METHOD AND COMPOSITION FOR RAPIDLY DEVELOPING LATENT FINGERPRINTS

BACKGROUND OF THE INVENTION

1. Field of the Invention

The present invention generally relates to the development of latent fingerprints such as might be found on various surfaces at the site of a criminal act so that the fingerprints can be powdered and lifted in a conventional manner for comparison with individuals who may be suspected of committing the criminal act. More particularly, the present invention relates to a method of and composition for quickly and rapidly developing latent fingerprints by subjecting the surface to the gas produced by a mixture of known and commercially available products including sodium bicarbonate, sulfur and cyanoacrylate ester, a commercially available adhesive sold under the trademark "Super Glue" or the trademark "Eastman 910".

2. Description of the Prior Art

Various techniques have been employed for developing latent fingerprints on various surfaces so that the developed fingerprints can be powdered and lifted for comparison purposes. The known methods have involved the expenditure of considerable time and usually is conducted at a lab rather than on site. One technique that has been developed is the subjection of the surface on which latent fingerprints exists to the gaseous fumes produced by cyanoacrylate ester or adhesive. However, the development of latent fingerprints by using these gaseous fumes usually requires several hours of time for the gaseous fumes to develop the latent fingerprints. Such delays are detrimental to efficient crime solution inasmuch as early fingerprint comparisons sometimes can eliminate certain suspects from consideration and identify persons at the scene of a crime or the like.

SUMMARY OF THE INVENTION

An object of the present invention is to provide a method of and composition for rapidly developing latent fingerprints on various surfaces in which the time required for developing latent fingerprints is materially reduced from a time period requiring several hours to a time period requiring only seconds.

Another object of the invention is to provide a composition for rapidly developing latent fingerprints on various surfaces including the combination of cyanoacrylate adhesive with sodium bicarbonate and sulfur which produces gaseous fumes that will rapidly develop latent fingerprints which are long lasting and capable of being lifted several times by employing conventional dusting or powder techniques used in lifting fingerprints for comparison purposes.

A further object of the invention is to provide a method of rapidly developing latent fingerprints on various surfaces including the step of subjecting the surfaces to gaseous fumes produced by a novel combination of known ingredients in which the fumes may be collected and placed into a small pressurized container so that they may be directed onto the surface at a crime site or the fumes may be formed interiorly of a large container so that the articles suspected of having latent fingerprints thereon may be inserted into the container so that the gaseous fumes will rapidly develop the latent fingerprints thereon.

Still another object of the invention is to provide a method of and composition for quickly and rapidly developing latent fingerprints on various surfaces such as glass, plastic, rubber, various metal surfaces such as copper, brass and the like and also paper and other materials which is quick and easy to use, effective for rapidly developing long lasting latent fingerprints which can be lifted several times if necessary with the present invention materially reducing the time required to develop and lift fingerprints for comparison purposes either at the site of the crime or in the laboratory.

DESCRIPTION OF THE PREFERRED EMBODIMENT

Assuming that some criminal act has occurred or for some other reason, it is desired to determine the identity of persons that may have grasped or otherwise placed their hand or fingers onto surfaces at a particular location, these surfaces are usually dusted or powdered and any fingerprints located will be lifted and compared with known fingerprints. Techniques have evolved by which the latent fingerprints on such surfaces can be developed to facilitate the fingerprints being lifted and compared. One technique that has been used is subjecting the surfaces to gaseous fumes having an eroding or etching effect on the surfaces involved in order to develop the latent fingerprints on such surfaces to facilitate those fingerprints being lifted and compared. Such techniques are relatively slow and usually require that the articles or surfaces involved be subjected to the gaseous fumes in a laboratory or the like. A specific technique which has been employed is subjecting the surfaces to the gasious fumes produced by cyanoacrylate ester or adhesive, such as that sold under the trademark "Super Glue" manufactured by Loctite Corporation of Cleveland, Ohio. Due to the slow release of gaseous fumes from this material, several hours time is required for the latent fingerprints to be developed. Such delays frequently hinder investigations of crimes and the like.

Essentially, the present invention involves the steps of mixing cyanoacrylate ester with sulfur and sodium bicarbonate which results in a much more rapid emission of gaseous fumes with the latent fingerprints being developed in seconds rather than hours. The fumes that are formed from this mixture causes the latent fingerprints to become visible to the eye in a very short time after the fumes come into contact with the latent fingerprints.

For use in the field or at the site of a crime, the gaseous fumes can be put into a can and placed under pressure and be used by anyone with the fumes being discharged onto the surfaces containing latent fingerprints so that the fingerprints will be quickly developed and easily lifted after powder is applied. For use in the laboratory, the mixture can be placed in a chamber along with the articles or surfaces in question or the fumes can be directed into such a chamber. In any event, the latent fingerprints developed by this method render the prints long lasting so that they can be lifted more than once. It is pointed out that this method should be practiced in a well ventilated area inasmuch as the gaseous fumes adversely affect the eyes and should not be inhaled in concentrated quantities.

One example of the composition of the present invention is the use of 12 grams of cyanoacrylate ester, 4 grams of sulfur and 12 grams of sodium bicarbonate. The cyanoacrylate may be mixed with the sulfur and sodium bicarbonate or the cyanoacrylate may be placed on a bed of the sulfur and sodium bicarbonate. In lab use, this mixture is placed in an open plate, tray, container or the like and placed inside of a larger container with the item or items on which fingerprints are to be developed. With the above quantity of materials, the container may have a volume capable of receiving 20 gallons of liquid with the above quantities of materials producing sufficient gaseous fumes to quickly develop latent fingerprints depending upon the type of material on which the latent fingerprints occur. If a larger container is used, a proportionately greater quantity of each of the ingredients should be used. Also, the mixture may be placed in a separate container communicated with the chamber in which the articles are placed through a pipe or the like if desired. The gaseous fumes produced may be pumped into a container under pressure and carried to a site in the field with the portable container including a manually operable valve and nozzle arrangement in order to direct the gaseous fumes onto the surfaces on which latent fingerprints may be found. When using the above example, it has been found that latent fingerprints on most plastic surfaces will begin to show prints about 5 seconds after being subjected to the gaseous fumes and the longest development time for latent fingerprints will be on paper surfaces which begins to show in 15-20 seconds and under any conditions or circumstances, will be developed within about 45 minutes. When using the above-mentioned 20-gal. container and the like, if additional articles are to be placed in the container, the same gaseous fumes can be used providing the door in the access opening of the container is rapidly opened and closed so that not much of the fumes egress from the container. It has been found that the same fumes can be used up to 3 hours since the mixture will continue to produce gaseous fumes and, of course, providing the access door to the container is not left open for long periods of time.

Additionally, this invention enables the development of latent fingerprints from the surface of living human skin by contacting another surface, such as plastic or the like, to the skin surface so that the latent fingerprints are transferred after which they are developed by using the present invention thereby eliminating any possible injury to the skin.

The present invention can be used as a two step method at the crime site. For example, a plastic bag of proper size may enclose the item or area to be developed, such as a handgun, long gun, doorknob or the like, and the mixture placed into the bag to develop any latent fingerprints thereon. The mixture without the cyanoacrylate ester can be placed in a sponge or on a fabric member and the cyanoacrylate added onto the surface thereof.

While the above example is preferred, it has also been found that gaseous fumes will be effectively produced and latent fingerprints effectively developed when the quantity of cyanoacrylate ester varies between 3 grams and 16 grams, the sulfur varies between 2 grams and 4 grams and the sodium bicarbonate varies between 8 grams and 16 grams.

The sodium bicarbonate referred to above is also known as baking soda, bicarbonate of soda and will have characteristics as set forth in the United States Pharmacopoeia. The sulfur also is a commercially available product in powder form as set forth in the U.S.P. The cyanoacrylate ester is an adhesive commercially available under the trademarks "Super Glue" and "Eastman 910" as set forth in the Condensed Chemical Dictionary, 8th Edition, published by Van Nostrand Reinhold Company, New York, New York.

It has also been found that sulfur can be eliminated from the mixture in certain instances. Further, sodium carbonate or sodium chloride either with or without sulfur may be substituted for the sodium bicarbonate. Also, either ethyl cyanoacrylate or methyl cyanoacrylate can be used except that methyl cyanoacrylate should not be used on plastic or rubber surfaces as it tends to deteriorate such surfaces. The addition of sulfur develops the background and valley areas of the fingerprints and provides better definition and higher ratios of sulfur delays development while lower ratios decreases development time but with less background development.

This method enables entire closed area, such as the interior of a room, automobile or the like to be developed in a very short time. Also, development time of the latent fingerprints provides an indication of the age of the fingerprints.

The following examples indicate some of the formulations which have been used with good success in developing latent fingerprints on various surfaces:

EXAMPLE I

Cyanoacrylate 12 grams—sodium bicarbonate 12 grams—sulfur 4 grams

EXAMPLE II

Cyanoacrylate 6 grams—sodium bicarbonate 10 grams—

EXAMPLE III

Cyanoacrylate 3 grams—sodium bicarbonate 10 grams—

EXAMPLE IV

Cyanoacrylate 3 grams—sodium bicarbonate 8 grams—sulfur 2 grams

EXAMPLE V

Cyanoacrylate 6 grams—sodium chloride 10 grams—

EXAMPLE VI

Cyanoacrylate 6 grams—sodium chloride 10 grams—sulfur 2 grams

The foregoing is considered as illustrative only of the principles of the invention. Further, since numerous modifications and changes will readily occur to those skilled in the art, it is not desired to limit the invention to the exact materials and ratios disclosed, and accordingly, all suitable modifications and equivalents may be resorted to, falling within the scope of the invention.

What is claimed as new is as follows:

1. The method of developing latent fingerprints on various surfaces comprising subjection of the surface on which a latent fingerprint exists to gaseous fumes produced by a mixture of cyanoacrylate ester, sulfur and sodium bicarbonate.

2. The method as defined in claim 1 together with the additional steps of powdering the developed fingerprints on the surface and lifting the fingerprints from the surface for comparison with known fingerprints.

3. The method as defined in claim 1 in which the surface and the mixture are placed in a closed container to subject the surface to the gas fumes.

4. The method as defined in claim 1 in which the fumes are pumped into a container under pressure with the container being carried to the site of the surface and the gas fumes discharged onto the surface for developing latent fingerprints thereon.

5. The method as defined in claim 1 in which the mixture includes 12 grams of cyanoacrylate ester, 4 grams of sulfur and 12 grams of sodium bicarbonate.

6. The method as defined in claim 1 in which the surface having the latent fingerprints thereon is selected from the group consisting of glass, plastic, rubber, metal and paper.

7. The method as defined in claim 1 wherein the mixture includes 3 grams to 16 grams of cyanoacrylate ester; 2 grams to 4 grams sulfur and 8 grams to 16 grams sodium bicarbonate.

8. A composition for developing latent fingerprints on various surfaces by subjecting the surfaces and fingerprints to gaseous fumes produced by the composition, said composition comprising a mixture of cyanoacrylate ester, and a material selected from the group consisting of sodium bicarbonate, sodium carbonate and sodium chloride.

9. The composition as defined in claim 8 wherein the mixture also includes sulfur.

10. The composition as defined in claim 9 wherein the mixture comprises 12 grams of cyanoacrylate ester, 4 grams to sulfur and 12 grams of sodium bicarbonate.

11. The composition as defined in claim 8 wherein the mixture includes 6 grams of cyanoacrylate ester and 10 grams of sodium bicarbonate.

12. The composition as defined in claim 8 wherein the mixture includes 3 grams of cyanoacrylate ester and 10 grams of sodium carbonate.

13. The composition as defined in claim 8 wherein the mixture includes 6 grams of cyanoacrylate ester and 10 grams of soidium chloride.

14. The composition of claim 13 together with 2 grams of sulfur.

15. The composition of claim 12 together with 2 grams of sulfur.

16. The method of developing latent fingerprints on a surface by subjecting the surface to gaseous fumes produced by a composition including a mixture of cyanoacrylate ester and a material selected from a group consisting of sodium bicarbonate, sodium carbonate and sodium chloride.

17. The method of developing latent fingerprints on a surface by subjecting the surface to gaseous fumes produced by a composition including a mixture of cyanoacrylate ester, a material selected from a group consisting of sodium bicarbonate, sodium carbonate and sodium chloride and sulfur.

* * * * *